(12) United States Patent
Tateno et al.

(10) Patent No.: US 11,806,702 B2
(45) Date of Patent: Nov. 7, 2023

(54) METHOD FOR PRODUCING OXIDE CATALYST AND METHOD FOR PRODUCING UNSATURATED NITRILE

(71) Applicant: ASAHI KASEI KABUSHIKI KAISHA, Tokyo (JP)

(72) Inventors: Eri Tateno, Tokyo (JP); Minoru Kadowaki, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 17/373,342

(22) Filed: Jul. 12, 2021

(65) Prior Publication Data

US 2021/0339239 A1    Nov. 4, 2021

Related U.S. Application Data

(63) Continuation of application No. 16/332,732, filed as application No. PCT/JP2017/032564 on Sep. 8, 2017, now Pat. No. 11,141,722.

(30) Foreign Application Priority Data

Sep. 13, 2016 (JP) ................. 2016-178885

(51) Int. Cl.

| | |
|---|---|
| *B01J 37/08* | (2006.01) |
| *B01J 23/30* | (2006.01) |
| *B01J 37/04* | (2006.01) |
| *C07C 253/24* | (2006.01) |
| *C07C 255/08* | (2006.01) |
| *B01J 23/00* | (2006.01) |
| *C07C 51/215* | (2006.01) |
| *B01J 37/00* | (2006.01) |
| *B01J 37/03* | (2006.01) |
| *C07B 61/00* | (2006.01) |

(52) U.S. Cl.
CPC ............ *B01J 37/08* (2013.01); *B01J 23/002* (2013.01); *B01J 23/30* (2013.01); *B01J 37/0027* (2013.01); *B01J 37/031* (2013.01); *B01J 37/04* (2013.01); *C07C 51/215* (2013.01); *C07C 253/24* (2013.01); *C07C 255/08* (2013.01); *B01J 2523/00* (2013.01); *B01J 2523/3706* (2013.01); *B01J 2523/3712* (2013.01); *B01J 2523/3787* (2013.01); *B01J 2523/44* (2013.01); *B01J 2523/55* (2013.01); *B01J 2523/56* (2013.01); *B01J 2523/68* (2013.01); *B01J 2523/69* (2013.01); *C07B 61/00* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 6,036,880 A | 3/2000 | Komada et al. | |
| 6,399,816 B1 | 6/2002 | Borchert et al. | |
| 2002/0072628 A1 | 6/2002 | Tu et al. | |
| 2003/0017944 A1 | 1/2003 | Hinago et al. | |
| 2008/0194871 A1 | 8/2008 | Dubois et al. | |
| 2008/0249328 A1 | 10/2008 | Kaduk et al. | |
| 2013/0053596 A1 | 2/2013 | Kato et al. | |
| 2013/0225862 A1 | 8/2013 | Tateno et al. | |
| 2013/0289298 A1 | 10/2013 | Tateno et al. | |
| 2016/0297753 A1 | 10/2016 | Ishii et al. | |
| 2016/0354761 A1 | 12/2016 | Ishii et al. | |

FOREIGN PATENT DOCUMENTS

| | | |
|---|---|---|
| CN | 10678326 A | 3/2010 |
| CN | 10992093 A | 3/2011 |
| CN | 103189139 A | 7/2013 |
| CN | 105813732 A | 7/2016 |
| CN | 105813747 A | 7/2016 |
| DE | 197 45 902 A1 | 4/1999 |
| EP | 2902105 A1 | 8/2015 |
| JP | 9-313943 A | 12/1997 |
| JP | 10-330343 A | 12/1998 |
| JP | 2001-520976 A | 11/2001 |
| JP | 2002-159853 A | 6/2002 |
| JP | 3938225 B2 | 6/2007 |
| JP | 2007-301470 A | 11/2007 |
| JP | 2008-537508 A | 9/2008 |

(Continued)

OTHER PUBLICATIONS

Al-Saeedi et al., "Bulk struture and catalytic properties of mixed Mo—V—Sb—Nb oxides for selective propane oxidation to acrylic acid," Journal of Catalysis (2003), vol. 215, pp. 108-115.
English translation of International Preliminary Report on Patentability and Written Opinion dated Mar. 28, 2019, in PCT/JP2017/032564 (Forms PCT/IB/326, PCT/IB/373, and PCT/ISA/237).
English translation of the Chinese Office Action for Chinese Application No. 201780054502.4, dated Apr. 27, 2021.
International Search Report for PCT/JP2017/032564 (PCT/ISA/210) dated Dec. 12. 2017.

(Continued)

*Primary Examiner* — Sheng H Davis
(74) *Attorney, Agent, or Firm* — Birch, Stewart, Kolasch & Birch, LLP

(57) ABSTRACT

The present invention relates to a method for producing an oxide catalyst containing Mo, V, Sb, and Nb, the method including a raw material preparation step of obtaining an aqueous mixed liquid containing Mo, V, Sb, and Nb, an aging step of subjecting the aqueous mixed liquid to aging at more than 30° C., a drying step of drying the aqueous mixed liquid, thereby obtaining a dried powder, and a calcination step of calcining the dried powder, thereby obtaining the oxide catalyst, and a method for producing an unsaturated nitrile or an unsaturated acid by using the catalyst.

3 Claims, No Drawings

(56) References Cited

FOREIGN PATENT DOCUMENTS

| JP | 2009-183897 A | 8/2009 |
|---|---|---|
| JP | 2010-526649 A | 8/2010 |
| JP | 4666334 B2 | 4/2011 |
| JP | 2013-226546 A | 11/2013 |
| JP | 2015171699 | * 10/2015 |
| WO | 2014050615 | * 3/2014 |

OTHER PUBLICATIONS

Modern Niobium-TantalumMetallurgy, edited by Kuo Quingwei, Wang Zhaoxin, Beijing: Metallurgical Industry Press, Jan. 31, 2009, pp. 126-129 (6 pages total).

Supplementary European Search Report dated Jun. 28, 2019, in European Patent Application No. 17850830.5.

Watanabe et al., "Comparative Study on the Catalytic Performance of Single-Phase Mo—V—O-Based Metal Oxide Catalysts in Propane Ammoxidation to Acrylonitrile," Ind. Eng. Chem. Res., vol. 45, No. 2, 2006 (published online Dec. 1, 2005), pp. 607-614.

Written Opinion of the International Searching Authority for PCT/JP2017/032564 (PCT/ISA/237) dated Dec. 12, 2017.

* cited by examiner

METHOD FOR PRODUCING OXIDE CATALYST AND METHOD FOR PRODUCING UNSATURATED NITRILE

CROSS-REFERENCE TO RELATED APPLICATIONS

This application is a Continuation application of co-pending application Ser. No. 16/332,732, filed on Mar. 12, 2019, which is the National Phase under 35 U.S.C. § 371 of International Application No. PCT/JP2017/032564, filed on Sep. 8, 2017, which claims the benefit under 35 U.S.C. § 119(a) to Patent Application No. 2016-178885, filed in Japan on Sep. 13, 2016, all of which are hereby expressly incorporated by reference into the present application.

TECHNICAL FIELD

The present invention relates to a method for producing an oxide catalyst and a method for producing an unsaturated nitrile.

BACKGROUND ART

Currently, unsaturated nitriles generally sold on the market are for the most part industrially produced through a catalytic ammoxidation reaction of an olefin, ammonia, and oxygen. On the other hand, in recent years, a method for producing an unsaturated nitrile corresponding to a raw material, the method using as the raw material an alkane such as propane or isobutane in place of the olefin and using a gas-phase catalytic ammoxidation reaction, has been drawing attention, and a large number of catalysts for use on that occasion have also been proposed.

For example, Patent Literature 1 describes a method for producing, as a catalyst for a gas-phase catalytic oxidation or gas-phase catalytic ammoxidation of propane or isobutane, a catalyst containing: at least one element selected from tellurium and antimony; molybdenum; vanadium; and niobium, in which a niobium raw material liquid containing niobium and a carboxylic acid is used.

In addition, as a catalyst for gas-phase catalytic oxidation or gas-phase catalytic ammoxidation of propane or isobutane, Patent Literature 2 describes a method for producing a catalyst containing: at least one element selected from tellurium and antimony; molybdenum; vanadium; and niobium, wherein precipitation of a niobium compound is prevented in a catalyst-producing step by adding a complex-forming agent such as hydrogen peroxide to a niobium raw material liquid.

In addition, Patent Literature 3 describes a method for producing a catalyst containing molybdenum, vanadium, and niobium, in which an aqueous mixed liquid containing the above-described elements is subjected to aging for 90 minutes or more and 50 hours or less under an atmosphere having an oxygen concentration of 1 to 25 vol %.

CITATION LIST

Patent Literature

Patent Literature 1: Japanese Patent No. 3938225
Patent Literature 2: Japanese Patent No. 4666334
Patent Literature 3: Japanese Patent Laid-Open No. 2009-183897

SUMMARY OF INVENTION

Technical Problem

However, according to the methods for producing a catalyst described in Patent Literatures 1 to 3, an ammoxidation reaction catalyst capable of enduring the use under particular conditions is obtained, but it cannot be deemed that the yield of an unsaturated nitrile, in a case where the resultant catalyst is used, is industrially sufficient. Further, there is a need for keeping a state in which all the components are uniformly dispersed in a solution containing a catalyst raw material while suppressing precipitation of Nb, which is a component that is hardly soluble, at the time of producing a catalyst, and therefore there is the following problem: it takes a long time to produce a catalyst.

The present invention has been made in consideration of the problems of the above-described conventional techniques, and an object of the present invention is to provide a method by which an oxide catalyst giving a high unsaturated nitrile yield can be obtained, and further, the oxide catalyst can be produced in a relatively short time without the need for introducing a complicated step and changing facilities.

Solution to Problem

The present inventors have conducted diligent studies to solve the problems of the conventional techniques to find that by following a method for producing an oxide catalyst, which is used for gas-phase contact oxidation or gas-phase contact ammoxidation of propane or isobutane and comprises particular components, comprises: a raw material preparation step; an aging step; a drying step; and a calcination step, wherein precipitation of niobium is facilitated in the preparation step and/or the aging step, an oxide catalyst exhibiting high performance can be produced in a relatively short time, thereby completing the present invention.

That is, the present invention is as follows.

1. A method for producing an oxide catalyst comprising Mo, V, Sb, and Nb, the method comprising:
   a raw material preparation step of obtaining an aqueous mixed liquid comprising Mo, V, Sb, and Nb;
   an aging step of subjecting the aqueous mixed liquid to aging at more than 30° C.;
   a drying step of drying the aqueous mixed liquid, thereby obtaining a dried powder; and
   a calcination step of calcining the dried powder, thereby obtaining the oxide catalyst,
   wherein, in the raw material preparation step and/or the aging step, precipitation of Nb is facilitated by performing at least one operation selected from the group consisting of the following (I) to (III):
   (I) in the raw material preparation step, the aqueous mixed liquid is prepared by mixing a Nb raw material liquid comprising Nb with a MoVSb raw material liquid comprising Mo, V, and Sb, wherein ammonia is added to at least one of the MoVSb raw material liquid, the Nb raw material liquid, and the aqueous mixed liquid such that a molar ratio in terms of $NH_3/Nb$ in the aqueous mixed liquid is adjusted to be 0.7 or more, and in the aging step, a temperature of the aqueous mixed liquid is adjusted to more than 50° C.;
   (II) in the aging step, a temperature of the aqueous mixed liquid is adjusted to more than 65° C.; and
   (III) in the raw material preparation step, the aqueous mixed liquid is prepared by mixing a Nb raw material liquid comprising Nb with a MoVSb raw material liquid comprising Mo, V, and Sb, wherein a molar ratio in terms of H$_2$O$_2$/Nb in the Nb raw material liquid is adjusted to less than 0.2, and in the aging step, a temperature of the aqueous mixed liquid is adjusted to more than 50° C.

2. The method for producing the oxide catalyst according to 1, wherein the oxide catalyst has a composition represented by the following formula (1):

$$MoV_aSb_bNb_cZ_dO_n \quad (1)$$

wherein Z represents at least one element selected from the group consisting of W, La, Ce, Yb, and Y; a, b, c, and d represent values in the ranges of $0.01 \leq a \leq 0.35$, $0.01 \leq b \leq 0.35$, $0.01 \leq c \leq 0.20$, and $0.00 \leq d \leq 0.10$, respectively; and n represents a value satisfying a balance of atomic valences.

3. The method for producing the oxide catalyst according to 1 or 2, wherein the oxide catalyst comprises 30% by mass or more and 70% by mass or less of a carrier based on a total amount of the oxide catalyst.

4. A method for producing an unsaturated nitrile, the method comprising: a step of obtaining the oxide catalyst by the method for producing the oxide catalyst according to any of 1 to 3; and a production step of producing an unsaturated nitrile through a gas-phase catalytic ammoxidation reaction of propane or isobutane in a presence of the produced oxide catalyst.

5. A method for producing an unsaturated acid, the method comprising: a step of obtaining the oxide catalyst by the method for producing the oxide catalyst according to any of 1 to 3; and a production step of producing an unsaturated acid through a gas-phase catalytic oxidation reaction of propane or isobutane in a presence of the produced oxide catalyst.

Advantageous Effects of Invention

According to the method for producing an oxide catalyst of the present invention, an oxide catalyst giving a high unsaturated nitrile yield can be obtained, and further, the oxide catalyst can be produced in a relatively short time without the need for introducing a complicated step and changing facilities.

DESCRIPTION OF EMBODIMENTS

Hereinafter, an embodiment for carrying out the present invention (hereinafter, simply referred to as "present embodiment") will be described in detail. The present embodiment, which will be described below, is an example for describing the present invention and is not intended to limit the present invention to the following contents. The present invention can be carried out by being appropriately modified within the range of the scope thereof.

[Method for Producing Oxide Catalyst]

A method for producing an oxide catalyst according to the present embodiment is a method for producing an oxide catalyst comprising Mo, V, Sb, and Nb, and comprises: a raw material preparation step of obtaining an aqueous mixed liquid (hereinafter, also referred to as "aqueous mixed liquid (N)") comprising Mo, V, Sb, and Nb; an aging step of subjecting the aqueous mixed liquid to aging at more than 30° C.; a drying step (hereinafter, also referred to as "step (c)") of drying the aqueous mixed liquid, thereby obtaining a dried powder; and a calcination step (hereinafter, also referred to as "step (d)") of calcining the dried powder, thereby obtaining the oxide catalyst, wherein in the raw material preparation step and/or the aging step, precipitation of Nb is facilitated by performing at least one operation selected from the group consisting of the following (I) to (III), namely an operation of facilitating precipitation of Nb is performed on the aqueous mixed liquid (N):

(I) in the raw material preparation step, the aqueous mixed liquid is prepared by mixing a Nb raw material liquid comprising Nb with a MoVSb raw material liquid comprising Mo, V, and Sb, wherein ammonia is added to at least one of the MoVSb raw material liquid, the Nb raw material liquid, and the aqueous mixed liquid such that a molar ratio in terms of NH$_3$/Nb in the aqueous mixed liquid is adjusted to be 0.7 or more, and in the aging step, a temperature of the aqueous mixed liquid is adjusted to more than 50° C.;

(II) in the aging step, a temperature of the aqueous mixed liquid is adjusted to more than 65° C.; and (III) in the raw material preparation step, the aqueous mixed liquid is prepared by mixing a Nb raw material liquid comprising Nb with a MoVSb raw material liquid comprising Mo, V, and Sb, wherein a molar ratio in terms of H$_2$O$_2$/Nb in the Nb raw material liquid is adjusted to less than 0.2, and in the aging step, a temperature of the aqueous mixed liquid is adjusted to more than 50° C.

According to the method for producing an oxide catalyst of the present embodiment, which is constituted in this way, an oxide catalyst giving a high unsaturated nitrile yield can be obtained, and further, the oxide catalyst can be produced in a relatively short time without the need for introducing a complicated step and changing facilities. The oxide catalyst obtained by the production method according to the present embodiment can be used suitably for a gas-phase catalytic oxidation reaction or gas-phase catalytic ammoxidation reaction of propane or isobutane.

In the raw material preparation step and/or the aging step in the present embodiment, the operation of facilitating precipitation of Nb is performed on the aqueous mixed liquid (N) as described above. "Precipitation of Nb is facilitated" is not particularly limited as long as Nb in the aqueous mixed liquid is precipitated to accelerate conversion of the aqueous mixed liquid into the form of a slurry, and can be performed, for example, through aspects of (I) to (III), which will be described in detail later. It is to be noted that precipitation of Nb can be checked, for example, by the oxidation-reduction potential of the aqueous mixed liquid, and it can be deemed that the precipitation is facilitated when a drop in the oxidation-reduction potential becomes fast. More specifically, it can be determined that precipitation of Nb has been facilitated when the oxidation-reduction potential of a mixed liquid (hereinafter, also referred to as "mixed liquid for measurement") of an aqueous mixed liquid (A), (A'), or (A") and an aqueous mixed liquid (N$_0$) or (N$_1$), which will be described later, satisfies at least one of the following a) and b) in a period of continuous 30 minutes from the time immediately after mixing until the time immediately before spray-drying (hereinafter, also referred to as "target period").

a) The potential of the mixed liquid for measurement at the point in time when the target period starts is lower than the potential of a standard liquid at the point in time when the target period starts, and the potential of the mixed liquid for measurement at the point in time when the target period ends is lower than the potential of the standard liquid at the point in time when the target period ends.

b) The amount of potential dropped, A, calculated as a difference between the value of the potential of the mixed liquid for measurement at the point in time when the target period starts and the potential of the mixed liquid for measurement at the point in time when the target period ends exceeds 1.2 times the amount of potential dropped, B, calculated as a difference between the value of the potential of the standard liquid at the point in time when the target period starts and the potential of the standard liquid at the point in time when the target period ends.

The "standard liquid" herein means an aqueous mixed liquid prepared under the same preparation conditions as in Comparative Example 1, which will be described later, namely an aqueous mixed liquid containing Mo, V, Sb, and Nb, the aqueous mixed liquid being obtained by adding hydrogen peroxide water to the Nb raw material liquid in an amount of 2.0 in terms of $H_2O_2/Nb$ without adding $NH_3$ water. In this context, the standard liquid is prepared in such a way as to obtain an oxide catalyst having the same composition as the oxide catalyst to be an object of evaluation with respect to the content of each metal element in the standard liquid. In addition, the "standard aging temperature" means 55° C. which is the temperature for aging carried out in Comparative Example 1. It is to be noted that the standard liquid is prepared by mixing the two aqueous mixed liquids at the simultaneous timing of preparing the mixed liquid for measurement, and the aging of the standard liquid is continued under the temperature condition which is the same as that in Comparative Example 1.

In the present embodiment, the amount of potential dropped, A, preferably exceeds 1.5 times the amount of potential dropped, B, and more preferably exceeds 2 times in the above-described b) from the viewpoint of moderately facilitating precipitation of Nb.

In the present embodiment, the raw material preparation step can include a preparation step (hereinafter, also referred to as "step (a)") which is a sub-step of preparing a MoVSb raw material liquid (hereinafter, also referred to as "aqueous mixed liquid (A)") comprising Mo, V, and Sb. In addition, the raw material preparation step can include a mixing step (hereinafter, also referred to as "step (b)") which is a sub-step of mixing the aqueous mixed liquid (A), the Nb raw material liquid comprising Nb, and, if necessary, a carrier raw material, thereby obtaining an aqueous mixed liquid (hereinafter, also referred to as "aqueous mixed liquid (N)"; or also referred to as "aqueous mixed liquid (B)" in particular when the aqueous mixed liquid further comprises a carrier raw material) comprising Mo, V, Sb, and Nb. Step (a) and step (b) will be described in detail later.

Further, the method for producing an oxide catalyst according to the present embodiment may further comprise a removal step (hereinafter, also referred to as "step (e)") of removing a protrusion existing at the surface of a particle of the oxide catalyst. Step (e) will be described in detail later.

In the present embodiment, "high unsaturated acrylonitrile yield" means that in a case where oxide catalysts each at least having the same composition as the composition represented by formula (1), which will be described later, are used, the yield of resultant unsaturated acrylonitrile is high.

[Step (a): Preparation Step]

In step (a) in the present embodiment, the aqueous mixed liquid (A) comprising Mo, V, and Sb is prepared. Examples of the preparation method include, but are not limited to, a method of mixing a Mo-containing raw material (hereinafter, also referred to as "Mo raw material"), a V-containing raw material (hereinafter, also referred to as "V raw material"), and an Sb-containing raw material (hereinafter, also referred to as "Sb raw material"), thereby preparing the aqueous mixed liquid (A). In addition, the method of mixing is not particularly limited, and known mixing methods can be used. In a case where step (a) is performed, a raw material comprising Nb (hereinafter, also referred to as "Nb raw material") in the present embodiment is preferably prepared separately from the aqueous mixed liquid (A). That is, in the present embodiment, the aqueous mixed liquid (A) preferably does not contain Nb.

Examples of the Mo raw material include, but are not limited to, ammonium heptamolybdate [$(NH_4)_6Mo_7O_{24} \cdot 4H_2O$], molybdenum trioxide [$MoO_3$], phosphomolybdic acid [$H_3PMo_{12}O_{40}$], silicomolybdic acid [$H_4SiMo_{12}O_{40}$], and molybdenum pentachloride [$MoCl_5$]. Among these, ammonium heptamolybdate [$(NH_4)_6Mo_7O_{24} \cdot 4H_2O$] is preferable. The Mo raw material may be these compounds or may be a solution obtained by dissolving the compounds in a solvent.

Examples of the V raw material include, but are not limited to, ammonium metavanadate [$NH_4VO_3$], vanadium pentoxide [$V_2O_5$], and vanadium chlorides [$VCl_4$, $VCl_3$]. Among these, ammonium metavanadate [$NH_4VO_3$] is preferable. The V raw material may be these compounds or may be a solution obtained by dissolving the compounds in a solvent.

Examples of the Sb raw material include, but are not limited to, antimony oxides [$Sb_2O_3$, $Sb_2O_5$], antimonious acid [$HSbO_2$], antimonic acid [$HSbO_3$], ammonium antimonate [$(NH_4)SbO_3$], antimony chloride [$Sb_2Cl_3$], organic acid salts such as a tartaric acid salt of antimony, and metal antimony. Among these, diantimony trioxide [$Sb_2O_3$] is preferable. The Sb raw material may be these compounds or may be a solution obtained by dissolving the compounds in a solvent.

[Step (b): Mixing Step]

In step (b) in the present embodiment, the aqueous mixed liquid (A), the Nb raw material, and, if necessary, the carrier raw material and a raw material for an additional element or elements constituting the catalyst are mixed to thereby obtain an aqueous mixed liquid (N). It is to be noted that the mixing method is not particularly limited, and known mixing methods can be used. It is to be noted that the carrier raw material is a raw material which becomes a carrier in the oxide catalyst.

The carrier raw material in the present embodiment preferably contains silica sol. Examples of silica sol include acidic sol and basic sol, but any silica sol may be used and basic silica sol is more preferable. The carrier raw material preferably contains 30% by mass or more, more preferably 30% by mass or more and 70% by mass or less, and still more preferably 40% by mass or more and 60% by mass or less, of silica sol in terms of $SiO_2$ based on the total amount (100% by mass) of the carrier raw material.

In step (b), it is preferable that the carrier raw material further contain powdery silica. This powdery silica becomes part of the silica raw material together with silica sol.

Examples of the carrier raw material include aluminum oxide, titanium oxide, and zirconium oxide in addition to silica sol, powdery silica, and the like. The carrier raw materials may be used singly, or two or more thereof may be used together. A preferred carrier raw material is silica.

In step (b), the silica sol is preferably 30% by mass or more and 70% by mass or less, more preferably 40% by mass or more and 60% by mass or less, and still more preferably 45% by mass or more and 55% by mass or less, in terms of $SiO_2$ based on the total amount (100% by mass) of silica sol and powdery silica. When the silica sol is 30% by mass or more, there is a tendency that deterioration of the attrition resistance of the oxide catalyst is thereby suppressed, and when the silica sol is 70% by mass or less, there is a tendency that deterioration of the performance of the oxide catalyst is thereby suppressed.

Examples of the Nb raw material include, but are not limited to, niobic acid, inorganic acid salts of niobium, and organic acid salts of niobium. Among these, niobic acid is preferable. Niobic acid is represented by formula $Nb_2O_5 \cdot nH_2O$ and is also called a niobium hydroxide or a niobium oxide compound.

The Nb raw material preferably contains water. The Nb raw material containing water is also referred to as a Nb raw material liquid. On this occasion, the ratio between water and Nb contained (Nb (mol)/Water (kg)) is more preferably set to 0.1 or more and 10 or less, still more preferably 0.3 or more and 5.0 or less, from the viewpoint of stabilizing the Nb raw material liquid or other viewpoints. In addition, the Nb raw material liquid may contain an organic acid salt or a free organic acid. The organic acid is not particularly limited, but oxalic acid is preferable. The molar ratio of the organic acid to niobium in the Nb raw material (organic acid/niobium) is preferably 1.0 or more and 4.0 or less.

The method of allowing the Nb raw material to contain water and the organic acid is not particularly limited, and water and the organic acid may be mixed in any order. In addition, the above-described mixing may be performed at any temperature as long as the temperature is equal to or more than a temperature at which the Nb raw material liquid containing water does not freeze and equal to or less than a temperature at which the Nb raw material liquid containing water is not boiled. However, from the viewpoint of operability of mixing and other viewpoints, the mixing is preferably performed at room temperature.

The Nb raw material liquid may further contain hydrogen peroxide water.

In the raw material preparation step and/or the aging step, an operation of facilitating precipitation of Nb is performed in the present embodiment. Conventionally, it has been considered that when precipitation of Nb is performed as slowly as possible to disperse Nb finely in the aqueous mixed liquid (N), the aqueous mixed liquid becomes more uniform, and the performance of a resultant catalyst also becomes more favorable.

In contrast, in the present embodiment, it has been found that even though precipitation of Nb is made fast as described above, a high-performance oxide catalyst is obtained in a relatively short time. Particularly in a case where various conditions in the operation are adjusted as will be described later, it has been found that these tendencies become remarkable.

The aspect (I) for facilitating precipitation of Nb is the following operation.

In the raw material preparation step, the aqueous mixed liquid is prepared by mixing the Nb raw material liquid comprising Nb with the MoVSb raw material liquid comprising Mo, V, and Sb, wherein ammonia is added to at least one of the MoVSb raw material liquid, the Nb raw material liquid, and the aqueous mixed liquid such that a molar ratio in terms of $NH_3/Nb$ in the aqueous mixed liquid is adjusted to be 0.7 or more, and in the aging step, the temperature of the aqueous mixed liquid is adjusted to more than 50° C.

The molar ratio is more preferably 0.8 or more and 7 or less, still more preferably 0.9 or more and 6 or less. By adding ammonia to the aqueous mixed liquid (N) such that the molar ratio in terms of $NH_3/Nb$ becomes 7 or less, there is a tendency that precipitation of Nb is facilitated in the range where the favorable catalyst performance is kept, there is a tendency that it can be prevented that the proper oxidation-reduction states of the metal components in the liquid cannot be maintained because $NH_3$ decomposes hydrogen peroxide which can be contained in the aqueous mixed liquid (N), and there is also a tendency that it can be prevented that the shape of the catalyst particle becomes distorted because the viscosity of the aqueous mixed liquid increases to make it hard to feed the aqueous mixed liquid in the drying step. It is to be noted that $NH_3$ at the time when the molar ratio in terms of $NH_3/Nb$ is calculated means the added ammonia and does not include an ammonium salt, such as ammonium heptamolybdate, ammonium metavanadate, or ammonium metatungstate, in the Mo raw material, the V raw material, the Sb raw material, the Nb raw material, or the Z raw material.

Ammonia is preferably added at each stage after preparing the aqueous mixed liquid (A), or is preferably added to the aqueous mixed liquid (N). That is, ammonia may be added at any stage after preparing the aqueous mixed liquid (A), and the order of addition of ammonia and addition of the Nb raw material liquid, silica sol, powdery silica raw material, and the like does not matter. Ammonia may be added immediately after obtaining the aqueous mixed liquid (A), may be added after Nb is mixed with the aqueous mixed liquid (A), may be added after silica sol is added to the aqueous mixed liquid (A), or may be added immediately before the drying step. In addition, ammonia may be added into the Nb raw material liquid or silica sol.

The form of ammonia to be added is not particularly limited, but ammonia water which is easy to handle is preferably used. Ammonia water can be used by appropriately selecting the concentration from among general concentrations.

The aspect (II) for facilitating precipitation of Nb is the following operation.

In the aging step, the temperature of the aqueous mixed liquid is adjusted to more than 65° C.

As will be described later, Nb forms a complex by the dicarboxylic acid and hydrogen peroxide to be stabilized in a dissolved state. By setting the temperature after adding Nb to more than 65° C., there is a tendency that decomposition of the complex progresses, so that precipitation of Nb can be effectively facilitated. From the viewpoint of moderately facilitating precipitation of Nb, the temperature after adding Nb is preferably set to more than 65° C. In addition, the above-described operation is particularly preferably performed as the step of subjecting the aqueous mixed liquid (N) to aging, which will be described later. Further, from the viewpoint of not allowing the precipitation to progress excessively and from the viewpoint of preventing the concentration of the other metal components in the aqueous mixed liquid from becoming excessively high due to evaporation or boiling of water, the temperature is preferably set to 100° C. or less, more preferably 90° C. or less, and still more preferably 80° C. or less. In addition, from the same reasons, the time to keep the temperature at more than 65° C. is preferably 1 minute or more and 5 hours or less.

The aspect (III) for facilitating precipitation of Nb is the following operation.

In the raw material preparation step, the aqueous mixed liquid is prepared by mixing the Nb raw material liquid comprising Nb with the MoVSb raw material liquid comprising Mo, V, and Sb, and here a molar ratio in terms of $H_2O_2/Nb$ in the Nb raw material liquid is adjusted to less than 0.2, and in the aging step, the temperature of the aqueous mixed liquid is adjusted to more than 50° C.

That is, in this aspect, a small amount of hydrogen peroxide may be added to the Nb raw material liquid, or hydrogen peroxide do not have to be added to the Nb raw material liquid. Hydrogen peroxide stabilizes Nb in a dissolved state by forming a complex with the Nb raw material, and therefore when the molar ratio is 1.8 or more, there is a tendency that precipitation of Nb is inhibited. On the other hand, when the molar ratio is set to less than 0.2, there is a tendency that the degree of stability of the complex composed of Nb, hydrogen peroxide, and the dicarboxylic acid is lowered, so that precipitation of Nb can be effectively facilitated. The molar ratio is more preferably set to less than 0.15, still more preferably less than 0.10.

In the present embodiment, at least one of the above-described aspects (I) to (III) may be selected and carried out, or a plurality of the above-described aspects (I) to (III) may be appropriately combined and carried out.

In step (a) and/or step (b), a raw material containing at least one element (hereinafter, also referred to as "component Z") selected from the group consisting of W, La, Ce, Yb, and Y may be further mixed.

The Z raw material is not limited to the following as long as it is a substance containing a component Z, and examples thereof include: a compound containing a component Z; and a metal of the component Z, the metal being made soluble by an adequate reagent. Examples of the compound containing a component Z include, but are not limited to, ammonium salts, nitric acid salts, carboxylic acid salts, ammonium carboxylates, peroxocarboxylic acid salts, ammonium peroxocarboxylates, halogenated ammonium salts, halides, acetylacetonate, and alkoxides. Among these, water-soluble raw materials such as nitric acid salts and carboxylic acid salts are preferable. It is to be noted that particularly when Z is W, the Z raw material is also referred to as a W raw material. The same applies to a La raw material, a Ce raw material, an Yb raw material, and an Y raw material.

In step (a) and/or step (b), the raw material ratio is preferably regulated such that the oxide catalyst obtained through step (d), which will be described later, has a composition represented by the following formula (1). By using the oxide catalyst having a composition represented by the following formula (1), there is a tendency that the yield of an unsaturated nitrile is further improved.

$$MoV_aSb_bNb_cZ_dO_n \quad (1)$$

wherein Z represents at least one element selected from the group consisting of W, La, Ce, Yb, and Y; a, b, c, and d represent values in the ranges of $0.01 \leq a \leq 0.35$, $0.01 \leq b \leq 0.35$, $0.01 \leq c \leq 0.20$, and $0.00 \leq d \leq 0.10$, respectively; n represents a value satisfying a balance of atomic valences; preferably $0.05 \leq a \leq 0.33$, $0.05 \leq b \leq 0.33$, $0.02 \leq c \leq 0.19$, and $0.001 \leq d \leq 0.09$; and more preferably $0.10 \leq a \leq 0.30$, $0.10 \leq b \leq 0.30$, $0.05 \leq c \leq 0.18$, and $0.002 \leq d \leq 0.08$.

The composition of the oxide catalyst which is obtained after step (d) may be different from the composition of the oxide catalyst which is finally obtained. That is, the composition of a protrusion, which will be described later, of the oxide catalyst and the composition of the main body of the oxide catalyst are different because, in a case where step (e) of removing this protrusion is included, the composition of the oxide catalyst before step (e) is changed after step (e). In step (a) and/or step (b), the composition ratio is preferably set in consideration of the change as well.

The "protrusion" in the present specification refers to matter that has oozed out at and/or adhered to the surface of a calcined body obtained through main calcination, which will be described later, or matter that has protruded from and/or adhered to the surface of a calcined body.

Hereinafter, in step (a) and/or step (b), description will be made taking as an example a case where the aqueous mixed liquid (B) comprising a Mo raw material, a V raw material, an Sb raw material, a Nb raw material, a carrier raw material, and a Z raw material is prepared using water as a solvent and/or a dispersion medium. However, step (a) and/or step (b) are not limited to this.

In step (a), the aqueous mixed liquid (A) can be prepared by adding the Mo raw material, the V raw material, the Sb raw material, and the Z raw material to water and heating a resultant mixture. When the aqueous mixed liquid (A) is prepared, the heating temperature and the heating time are preferably adjusted in such a way as to create a state in which respective raw materials are sufficiently soluble. Specifically, the heating temperature is preferably 70° C. or more and 100° C. or less, and the heating time is preferably 30 minutes or more and 5 hours or less. On this occasion, the aqueous mixed liquid (A) is preferably being stirred such that the raw materials easily dissolve. On this occasion, the atmosphere for preparing the aqueous mixed liquid (A) may be an air atmosphere but can be a nitrogen atmosphere from the viewpoint of adjusting the oxidation number of the resultant oxide catalyst. The aqueous mixed liquid (A) which is in a state after completion of the above-described heating is also referred to as an aqueous mixed liquid (A'). The temperature of the aqueous mixed liquid (A') is preferably held at 20° C. or more and 80° C. or less, and more preferably held at 40° C. or more and 80° C. or less. When the temperature of the aqueous mixed liquid (A') is 20° C. or more, there is a tendency that the precipitation of metal species dissolving in the aqueous mixed liquid (A') is thereby unlikely to occur.

Subsequently, a carrier raw material containing silica sol can be added to the aqueous mixed liquid (A) or the aqueous mixed liquid (A'). Among these, silica sol is preferably added to the aqueous mixed liquid (A'). Silica sol functions as a carrier when it is made into an oxide catalyst. The temperature at the point in time when silica sol is added is preferably 80° C. or less. In a case where silica sol is added at 80° C. or less, there is a tendency that the stability of the silica sol is relatively high to suppress gelation of the aqueous mixed liquid (B). The timing of adding silica sol may be at the point in time when aging is started, which will be described later, may be in the middle of aging, or may be immediately before drying the aqueous mixed liquid (B).

Further, from the viewpoint of adjusting the oxidation number of a complex oxide in the resultant oxide catalyst, if necessary, an appropriate amount of hydrogen peroxide water ($H_2O_2$) is preferably added to the aqueous mixed liquid (A) or the aqueous mixed liquid (A'). With respect to the timing of adding hydrogen peroxide water, hydrogen peroxide water may be added to the aqueous mixed liquid (A) or the aqueous mixed liquid (A') itself, may be added in the middle of preparing the aqueous mixed liquid (A) or the aqueous mixed liquid (A'), or may be added before or after adding silica sol. On this occasion, from the viewpoint of adjusting the oxidation number of the resultant oxide catalyst in a proper range, the amount of addition of hydrogen peroxide water is 0.01 or more and 5.0 or less, more preferably 0.5 or more and 3.0 or less, and still more preferably 1.0 or more and 2.5 or less as a molar ratio of hydrogen peroxide water to Sb ($H_2O_2/Sb$).

Conditions (heating temperature and heating time) of a treatment which can be performed on the aqueous mixed liquid after adding hydrogen peroxide water to the aqueous mixed liquid (A) or the aqueous mixed liquid (A') (hereinafter, also referred to as "aqueous mixed liquid (A")") are preferably adjusted in such a way as to create a state in which a liquid-phase oxidation reaction by hydrogen peroxide can sufficiently progress. Specifically, the heating temperature is preferably 20° C. or more and 80° C. or less, and the heating time is preferably 5 minutes or more and 4 hours or less. Similarly, the number of revolutions during stirring at the time of heating can be adjusted to a moderate number of revolutions at which hydrogen peroxide water is uniformly mixed in the liquid and a sufficient liquid-phase oxidation reaction by hydrogen peroxide water easily progresses. From the viewpoint of allowing the liquid-phase oxidation reaction by hydrogen peroxide water to progress uniformly and sufficiently, the stirring state is preferably kept during heating.

Next, the Nb raw material liquid is preferably prepared as an aqueous mixed liquid ($N_0$) by heating and stirring the Nb raw material and a dicarboxylic acid in water. Examples of the dicarboxylic acid include, but are not limited to, oxalic acid $[(COOH)_2]$. Subsequently, an aqueous mixed liquid ($N_1$) is preferably prepared by adding hydrogen peroxide water to the aqueous mixed liquid ($N_0$). On this occasion, the molar ratio of hydrogen peroxide water to Nb ($H_2O_2$/Nb) in the aqueous mixed liquid ($N_1$) is preferably set to less than 0.2 from the viewpoint of moderately facilitating precipitation of Nb, properly regulating the oxidation-reduction states of constituent elements of the oxide catalyst, making the catalyst performance of the resultant oxide catalyst proper, and other viewpoints.

Subsequently, the aqueous mixed liquid (N) can be obtained by mixing the aqueous mixed liquid (A), the aqueous mixed liquid (A'), or the aqueous mixed liquid (A") with the aqueous mixed liquid ($N_0$) or the aqueous mixed liquid ($N_1$) in conformity to the aimed composition. On this occasion, ammonia, the W raw material, or powdery silica may further be mixed.

In addition, the silica raw material may be mixed in the aqueous mixed liquid ($N_0$) or the aqueous mixed liquid ($N_1$) in advance. The order of mixing the aqueous mixed liquid ($N_0$) or the aqueous mixed liquid ($N_1$) with the silica raw material is not particularly limited. The silica raw material may be added to the aqueous mixed liquid ($N_0$) or the aqueous mixed liquid ($N_1$), or the aqueous mixed liquid ($N_0$) or the aqueous mixed liquid ($N_1$) may be added to the silica raw material. Among these, the silica raw material may more preferably be added to the aqueous mixed liquid ($N_0$) or the aqueous mixed liquid ($N_1$) from the viewpoint of suppressing precipitation of Nb in the aqueous mixed liquid ($N_0$) or the aqueous mixed liquid ($N_1$). In addition, a resultant mixture may be left to stand or stirred after the addition, and further, an ultrasonic treatment may be performed with a homogenizer or the like. On this occasion, part of the other metal raw materials may be added to the aqueous mixed liquid ($N_0$) or the aqueous mixed liquid ($N_1$) in advance, or part of the other metal raw materials may be added to the silica raw material in advance. The other metal raw materials refer to the Mo raw material, the V raw material, the Sb raw material, the W raw material, and the Z raw material. In addition, the amount of addition of the other metal raw materials on this occasion is preferably less than 50% by mass, more preferably 0.0% by mass or more and 40% by mass or less, and still more preferably 0.0% by mass or more and 30% by mass or less, based on the total amount of the metal raw materials which are finally added.

From the viewpoint of making the catalyst performance proper, powdery silica is preferably added to the "aqueous mixed liquid (A")" or a "solution obtained by mixing the W raw material into the aqueous mixed liquid (B)." In addition, powdery silica can be added as it is, but is more preferably added as a liquid in which the powdery silica is dispersed in water, that is, as a powdery silica-containing suspension. The concentration of powdery silica in the powdery silica-containing suspension on this occasion is preferably 1.0% by mass or more and 30% by mass or less, and more preferably 3.0% by mass or more and 20% by mass or less. When the concentration of powdery silica is 1.0% by mass or more, there is a tendency that it can be thereby suppressed that the shape of the catalyst particle becomes distorted due to a low viscosity of the aqueous mixed liquid (B). In addition, there is a tendency that occurrence of a depression in the catalyst particle can also be suppressed. When the concentration of powdery silica is 30% by mass or less, there is a tendency that gelation of the aqueous mixed liquid (B) and clogging of the aqueous mixed liquid (B) in piping, the gelation and the clogging being attributable to a high viscosity of the aqueous mixed liquid (B), can be thereby suppressed, and there is a tendency that the dried powder can be thereby easily obtained. Further, there is a tendency that the performance of the oxide catalyst is further improved.

Ammonia can be added to the aqueous mixed liquid (A), (A'), (A"), or (B) in order to facilitate precipitation of Nb. From the viewpoint of properly keeping the dissolution state of the metals in the aqueous mixed liquid (A), the viewpoint of effectively facilitating precipitation of Nb, and other viewpoints, ammonia is more preferably added to the aqueous mixed liquid (B). Part of ammonia may be added simultaneously with silica sol. The timing of addition to the aqueous mixed liquid (B) can be appropriately adjusted.

As the amount of $NH_3$ to be added, addition in an amount that makes the molar ratio in terms of $NH_3$/Nb in the aqueous mixed liquid (B) 0.7 or more and 7 or less is preferable. The molar ratio is more preferably 0.8 or more and 6 or less, and still more preferably 0.9 or more and 5.5 or less. By setting the molar ratio to 7 or less, precipitation of Nb can be facilitated in the range where favorable catalyst performance is kept, it can be prevented that the proper oxidation-reduction states of the metal components in the liquid cannot be maintained because $NH_3$ decomposes hydrogen peroxide in the aqueous mixed liquid, and it can be prevented that the shape of the catalyst particle becomes distorted because the viscosity of the aqueous mixed liquid increases to make it hard to feed the aqueous mixed liquid in the drying step.

[Aging Step]

In the present embodiment, the resultant aqueous mixed liquid (B) is provided for an aging treatment. Aging of the aqueous mixed liquid (B) refers to leaving the aqueous mixed liquid (B) to stand or stirring the aqueous mixed liquid (B) for a predetermined time under the temperature condition at more than 30° C. The aging time is preferably 5 minutes or more and 50 hours or less, and more preferably 5 minutes or more and 3 hours or less. When the aging time is in the range, there is a tendency that the aqueous mixed liquid (B) having a suitable oxidation-reduction state (potential) becomes easily formed, and the catalyst performance of a resultant complex oxide is further improved.

In a case where the oxide catalyst is industrially produced via drying with a spray-drier herein, the treatment speed of the spray drier usually controls the speed of production, and there is a tendency that it takes time for the spray-drying of all the aqueous mixed liquid (B) to be completed after part of the mixed liquid is spray-dried. During the spray-drying, aging of the aqueous mixed liquid which has not been subjected to the spray-drying treatment yet is continued. Accordingly, the aging time not only includes the aging time before drying in step (c), which will be described later, but also includes the time from the start to the completion of drying.

In addition, the aging temperature is set to more than 30° C. from the viewpoints of preventing condensation of the Mo component or precipitation of the metal oxide due to V and the other metal species or a plurality of metals, making the oxidation states of Mo, V, and the other metal species proper, and allowing precipitation of Nb to progress moderately. The aging temperature is more preferably set to more than 50° C., and still more preferably more than 54° C. In addition, the aging temperature is preferably more than 65° C. from the viewpoint of forming the aqueous mixed liquid (B) of a preferred embodiment while allowing the speed of precipitation of Nb due to hydrolysis of a complex containing Nb and hydrogen peroxide to fall within a proper range, and is preferably set to 100° C. or less, more preferably 90° C. or less, and still more preferably 80° C. or less in order not to allow the precipitation to progress excessively and in order to prevent the concentration of the other metal components in the aqueous mixed liquid from becoming excessively high due to evaporation/boiling of water. That is, adjusting the temperature of the aqueous mixed liquid in the second preferred aspect described above is preferably performed in the aging step. By extending the aging time, raising the temperature of aging, or combining and performing these, the catalyst can be further reduced during calcination.

In addition, according to diligent studies conducted by the present inventors, it has been found that there is a tendency that the reduction rate of the catalyst after calcination and the oxidation-reduction potential of the aqueous mixed liquid (B) have a certain correlation. When the oxidation-reduction potential of the aqueous mixed liquid (B) becomes high, the catalyst after calcination leans toward an oxidation direction, and when the oxidation-reduction potential of the aqueous mixed liquid (B) becomes low, the catalyst after calcination leans toward a reduction direction. The oxidation-reduction potential of the aqueous mixed liquid (B) can be measured by using, but not particularly limited to, a potentiometer sold on the market. Specifically, the oxidation-reduction potential is measured by the method described in Examples, which will be described later.

[Step (c): Drying Step]

Step (c) of the present embodiment is a step of drying the aqueous mixed liquid (N), thereby obtaining a dried powder. Drying can be performed by known methods and can also be conducted, for example, by spray-drying or evaporation to dryness. In a case where a fluidized bed reaction system is adopted in a gas-phase catalytic oxidation reaction or gas-phase catalytic ammoxidation reaction in which the oxide catalyst is used, a fine, spherical dried powder is preferably obtained in step (c) from the viewpoint of making the fluidity in a reactor into a preferred state, or other viewpoints. From the viewpoint of obtaining a fine, spherical dried powder, spray-drying is preferably adopted. Nebulization in the spray-drying method may be any of a centrifugal system, a two-fluid nozzle system, and a high-pressure nozzle system. As a heat source for drying, air heated with steam, an electric heater, or the like can be used.

The spray velocity, the rate of feeding the aqueous mixed liquid (B), the number of revolutions of an atomizer in the case of a centrifugal system, and the like are preferably adjusted such that the size of a resultant dried powder becomes suitable. The average particle diameter of the dried powder is preferably 35 μm or more and 75 μm or less, more preferably 40 μm or more and 70 μm or less, and still more preferably 45 μm or more and 65 μm or less. The average particle diameter does not change so much even after calcination. Examples of the method of adjusting the average particle diameter of the dried powder include a method of performing classification, which will be described in Examples.

[Step (d): Calcination Step]

In step (d) of the present embodiment, the dried powder is calcined, and an oxide catalyst is thereby obtained. As a calcination apparatus for calcining the dried powder, a rotary furnace (rotary kiln) for example can be used. The shape of a calcination vessel in which the dried powder is calcined is not particularly limited, but the calcination vessel is preferably pipe-shaped (calcination pipe) from the viewpoint of enabling continuous calcination, and more preferably cylindrically shaped. As a heating system, an external heating type is preferable from the viewpoint of easiness of adjusting the calcination temperature in such a way as to make a temperature-raising pattern preferable, and an electric furnace can be suitably used as an external heat source. The size, the material, and the like of the calcination pipe can be appropriately selected according to the calcination conditions and the quantity of production.

In step (d), the calcination is desirably performed by being divided into two stages. When the first calcination is referred to as fist-stage calcination, and the latter calcination is referred to as main calcination, it is preferable that the pre-stage calcination be performed in a temperature range of 250° C. or more and 400° C. or less, and the main calcination be performed in a temperature range of 450° C. or more and 700° C. or less. The pre-stage calcination and the main calcination may be performed continuously, or the main calcination may be performed afresh after the pre-stage calcination is once completed. Alternatively, each of the pre-stage calcination and the main calcination may be divided into several stages.

With respect to the calcination atmosphere, the calcination may be performed in an air atmosphere or under air circulation, but from the viewpoint of adjusting the oxidation-reduction state into a preferred one, at least part of the calcination is preferably performed while an inert gas, such as nitrogen, which does not substantially contain oxygen is circulated. In a case where the calcination is performed batch-wise, the supply rate of the inert gas is preferably 50 NL/hr. or more, more preferably 50 NL/hr. or more and 5000 NL/hr. or less, and still more preferably 50 NL/hr. or more and 3000 NL/hr. or less per kg of the dried powder from the viewpoint of adjusting the oxidation-reduction state into a preferred one. The "NL" herein means volume of a gas measured at the normal temperature and pressure conditions, namely at 0° C. and 1 atm.

The reduction rate of a calcined body (pre-stage calcined body) after the pre-stage calcination is preferably 7.0% or more and 15% or less, more preferably 8.0% or more and 12% or less, and still more preferably 9.0% or more and 12% or less. When the reduction rate is in this range, there is a tendency that the activity of the oxide catalyst is thereby further improved, and the catalyst production efficiency is thereby further improved. Examples of a method of controlling the reduction rate in a desired range include, but are not limited to, a method of changing the pre-stage calcination temperature, a method of adding an oxidative component such as oxygen into the atmosphere during the calcination, and a method of adding a reductive component into the atmosphere during the calcination. In addition, these may be combined.

[Step (e): Removal Step]

In step (e) optionally performed in the present embodiment, a protrusion existing at the surface of a particle of the oxide catalyst is removed. Most of the protrusions are protruded crystals of an oxide or other impurities. Particularly in the case of a calcined body containing a plurality of metals, an oxide having a composition which is different from that of the crystal which forms most part of the calcined body may be formed in some cases in a form such that the oxide has oozed out of the main body part of the calcined body. There is a tendency that such a protrusion becomes a factor of lowering the fluidity. Therefore, by removing the protrusion from the surface of the oxide catalyst, there is a tendency that the performance of the oxide catalyst gets higher. In a case where the removal of the protrusion is performed in a gram scale, the apparatus described below can be used. That is, a perpendicular tube provided with a holed board having at least one hole at the bottom portion thereof and having a paper filter installed at the upper portion can be used. By loading the calcined body into this perpendicular tube and circulating air from below, air flows from each hole to facilitate contact among calcined bodies, and the removal of the protrusion is performed.

[Oxide Catalyst]

The oxide catalyst according to the present embodiment is obtained by the above-described method for producing an oxide catalyst. The resultant oxide catalyst preferably has a composition represented by the following formula (1).

$$MoV_aSb_bNb_cZ_dO_n \quad (1)$$

wherein Z represents at least one element selected from the group consisting of W, La, Ce, Yb, and Y; a, b, c, and d represent values in the ranges of $0.01 \leq a \leq 0.35$, $0.01 \leq b \leq 0.35$, $0.01 \leq c \leq 0.20$, and $0.00 \leq d \leq 0.10$, respectively; and n represents a value satisfying a balance of atomic valences.

The composition of the oxide catalyst can be measured with fluorescent X-ray analysis (trade name "RIX1000" manufactured by Rigaku Corporation, Cr tube, tube voltage of 50 kV, tube current of 50 mA).

The oxide catalyst preferably comprises 30% by mass or more and 70% by mass or less of a carrier based on the total amount (100% by mass) of a composite body of the oxide catalyst and the carrier. To obtain the oxide catalyst that is in such a range, the oxide catalyst preferably uses 30% by mass or more and 70% by mass or less, as the total amount, of silica, such as silica sol and powdery silica, in terms of $SiO_2$ based on the total amount of the composite body, and the oxide catalyst may more preferably use 40% by mass or more and 60% by mass or less of silica and may still more preferably use 45% by mass or more and 55% by mass or less of silica. When the oxide catalyst comprises 30% by mass or more of the carrier based on the total amount of the composite body, there is a tendency that the strength of the composite body comprising the oxide catalyst is thereby further improved, and when the oxide catalyst comprises 70% by mass or less of the carrier, there is a tendency that the oxide catalyst thereby has a higher activity.

The content of the carrier in the oxide catalyst can be determined, for example, by measurement with fluorescent X-ray analysis (trade name "RIX1000" manufactured by Rigaku Corporation, Cr tube, tube voltage of 50 kV, tube current of 50 mA).

[Method for Producing Unsaturated Nitrile or Unsaturated Acid]

The method for producing an unsaturated nitrile according to the present embodiment comprises: a step of obtaining an oxide catalyst by the method for producing an oxide catalyst according to the present embodiment; and a production step of producing an unsaturated nitrile through a gas-phase catalytic ammoxidation reaction of propane or isobutane in the presence of the produced oxide catalyst. In addition, the method for producing an unsaturated acid according to the present embodiment comprises: a step of obtaining an oxide catalyst by the method for producing an oxide catalyst according to the present embodiment; and a production step of producing an unsaturated acid through a gas-phase catalytic oxidation reaction of propane or isobutane in the presence of the produced oxide catalyst. In addition, the production step is preferably a step of producing an unsaturated nitrile through a gas-phase catalytic ammoxidation reaction of propane or isobutane. Hereinafter, a method for producing acrylonitrile as the unsaturated nitrile using the oxide catalyst according to the present embodiment filled in a reactor will be described.

<Gas-Phase Catalytic Oxidation Reaction and Gas-Phase Catalytic Ammoxidation Reaction>

Propane or isobutane, and oxygen are used for a gas-phase catalytic oxidation reaction, and propane or isobutane; ammonia; and oxygen are used for a gas-phase catalytic ammoxidation reaction. Among them, propane and ammonia do not necessarily have to be of high purity, and may be industrial-grade gasses such as propane containing 3% by volume of an impurity such as ethane, ethylene, n-butane, or isobutane; and ammonia containing 3% by volume of an impurity such as water. Examples of oxygen include, but are not limited to: air, oxygen-enriched air, and pure oxygen; and gases obtained by diluting these with an inert gas such as helium, argon, carbon dioxide, or nitrogen, or water vapor. Among these, in the case of use in an industrial scale, air is preferable because of simplicity.

The reaction conditions in the gas-phase catalytic oxidation reaction are not particularly limited, and examples thereof include the following conditions. The molar ratio of oxygen to be supplied for the reaction to propane or isobutane, (oxygen/(propane and isobutane)), is preferably 0.1 or more and 6.0 or less, and more preferably 0.5 or more and 4.0 or less. The reaction temperature is preferably 300° C. or more and 500° C. or less, and more preferably 350° C. or more and 500° C. or less. The reaction pressure is preferably $5.0 \times 10^4$ Pa or more and $5.0 \times 10^5$ Pa or less, and more preferably $1.0 \times 10^5$ Pa or more and $3.0 \times 10^5$ Pa or less. The contact time is preferably 0.1 sec·g/cm³ or more and 10 sec·g/cm³ or less, and more preferably 0.5 sec·g/cm³ or more and 5.0 sec·g/cm³ or less. By setting the reaction conditions to the ranges, there is a tendency that production of a by-product is further suppressed, and the yield of an unsaturated nitrile can be further improved.

In the present embodiment, the contact time is defined by the following expression.

$$\text{Contact time (sec·g/cm}^3) = (W/F) \times 273/(273+T)$$

W, F, and T herein are defined as follows.

W=amount (g) of catalyst filled

F=flow rate (Ncm³/sec) of raw material mixed gas at the normal state (0° C., $1.013 \times 10^5$ Pa)

T=reaction temperature (° C.)

The conversion rate of alkane such as propane or isobutane, and the unsaturated acid or unsaturated nitrile yield follow the following definition.

Conversion rate (%) of alkane=(number of moles of alkane reacted)/(number of moles of alkane supplied)×100

Unsaturated acid or unsaturated nitrile yield (%)= (number of moles of unsaturated acid or unsaturated nitrile produced)/(number of moles of alkane supplied)×100

The reaction conditions in the gas-phase catalytic ammoxidation reaction are not particularly limited, and examples thereof include the following conditions. The molar ratio of oxygen to be supplied for the reaction to propane or isobutane, (oxygen/(propane and isobutane)), is preferably 0.1 or more and 6.0 or less, and more preferably 0.5 or more and 4.0 or less. The molar ratio of ammonia to be supplied for the reaction to propane or isobutane, (ammonia/(propane and isobutane)), is preferably 0.3 or more and 1.5 or less, and more preferably 0.7 or more and 1.2 or less. The reaction temperature is preferably 320° C. or more and 500° C. or less, and more preferably 370° C. or more and 460° C. or less. The reaction pressure is preferably $5.0 \times 10^4$ Pa or more and $5.0 \times 10^5$ Pa or less, and more preferably $1.0 \times 10^5$ Pa or more and $3.0 \times 10^5$ Pa or less. The contact time is preferably 0.1 sec·g/cm$^3$ or more and 10 sec·g/c$^3$ or less, and more preferably 0.5 sec·g/cm$^3$ or more and 5.0 sec·g/cm$^3$ or less. By setting the reaction conditions to the ranges, there is a tendency that production of a by-product is further suppressed, and the yield of an unsaturated nitrile can be further improved.

As a reaction system in the gas-phase catalytic oxidation reaction and the gas-phase catalytic ammoxidation reaction, known systems such as a fixed bed, a fluidized bed, and a moving bed can be adopted. Among these, a fluidized bed reactor in which the heat of reaction is easily removed is preferable. In addition, the gas-phase catalytic ammoxidation reaction may be a single current type or a recycling type.

EXAMPLES

Hereinafter, the present embodiment will be described in further detail giving specific Examples and Comparative Examples, but the present embodiment is not limited by the following Examples and Comparative Examples within a range not exceeding the scope thereof. Measurement and evaluation of various physical properties in the Examples and the Comparative Examples, which will be described later, were performed according to the following methods.

(Preparation Example) Aqueous Mixed Liquid ($N_0$)

An aqueous mixed liquid ($N_0$) was prepared according to the following method. Into 10 kg of water, 1.420 kg of niobic acid containing 79.8% by mass of $Nb_2O_5$ and 5.134 kg of oxalic acid dihydrate ($H_2C_2O_4 \cdot 2H_2O$) were mixed. The molar ratio of oxalic acid/niobium added was 4.8, and the concentration of niobium added was 0.52 mol/kg. This liquid was heated and stirred at 95° C. for 2 hours to thereby obtain a mixed liquid containing niobium dissolved therein. This mixed liquid was left to stand and cooled with ice, and thereafter a solid was separated by suction filtration to obtain a uniform niobium mixed liquid. The molar ratio of oxalic acid/niobium in this niobium mixed liquid was found to be 2.340 by the analysis described below. The resultant niobium mixed liquid was used as an aqueous mixed liquid ($N_0$) in producing oxide catalysts of Examples 1 to 12 and Comparative Examples 1 to 4 below.

(Physical Property 1) Concentration of Niobium and Concentration of Oxalic Acid

Into a melting pot, 10 g of the aqueous mixed liquid ($N_0$) obtained above was precisely weighed, and was dried at 95° C. overnight, and thereafter a heat treatment was performed at 600° C. for 1 hour to obtain 0.8125 g of $Nb_2O_5$. From this result, the concentration of niobium was found to be 0.611 mol (Nb)/kg (aqueous mixed liquid ($N_0$)). In addition, 3 g of this aqueous mixed liquid ($N_0$) was precisely weighed into a 300-mL glass beaker, 200 mL of approximately 80° C. hot water was added thereto, and subsequently 10 mL of 1:1 sulfuric acid was added thereto. A resultant mixed liquid was titrated under stirring using 1/4 N $KMnO_4$ while keeping the liquid temperature at 70° C. on a hot stirrer. A point where a slight, light pink color by $KMnO_4$ continued for approximately 30 seconds or more was determined to be an end point. The concentration of oxalic acid was determined from the titer by calculation according to the following formula and was found to be 1.430 mol (oxalic acid)/kg (aqueous mixed liquid ($N_0$)).

$$2KMnO_4 + 3H_2SO_4 + 5H_2C_2O_4 \rightarrow K_2SO_4 + 2MnSO_4 + 10CO_2 + 8H_2O$$

(Physical Property 2) Oxidation-Reduction Potential of Aqueous Mixed Liquids (B)

The oxidation-reduction potential of the aqueous mixed liquids (B) was measured using a potentiometer sold on the market (manufactured by DKK-TOA CORPORATION).

(Physical Property 3) Composition of Oxide Catalysts

The composition of the oxide catalysts was measured with fluorescent X-ray analysis (trade name "RIX1000" manufactured by Rigaku Corporation, Cr tube, tube voltage of 50 kV, tube current of 50 mA).

(Physical Property 4) Amount of Carrier

The amount of a carrier is defined as the amount of the carrier (% by mass) based on the total amount (100% by mass) of the oxide catalyst obtained in each of the Examples and the Comparative Examples, which will be described later, and the resultant oxide catalyst was subjected to measurement by fluorescent X-ray analysis (trade name "RIX1000" manufactured by Rigaku Corporation, Cr tube, tube voltage of 50 kV, tube current of 50 mA) to determine the amount of the carrier.

(Evaluation) Yield of Acrylonitrile (Unsaturated Nitrile), Conversion Rate of Propane In the Examples and the Comparative Examples, the yield of acrylonitrile was determined as follows. A gas of acrylonitrile the concentration of which was already known was analyzed by gas chromatography (GC: product name "GC2014" manufactured by SHIMADZU CORPORATION) to get a calibration curve in advance, and thereafter a gas produced through the ammoxidation reaction was quantitatively injected into the GC to measure the number of moles of acrylonitrile produced. The yield of acrylonitrile was determined from the measured number of moles of acrylonitrile according to the following expression.

Yield (%) of acrylonitrile=(number of moles of acrylonitrile produced)/(number of moles of propane supplied)×100

In addition, the conversion rate of propane was determined as follows. A gas of propane the concentration of which was already known was analyzed by the GC to get a calibration curve in advance, and thereafter a gas produced through the ammoxidation reaction was quantitatively injected into the GC to measure the number of moles of unreacted propane. The conversion rate of propane was determined from the measured number of moles of unreacted propane according to the following expression.

Conversion rate (%) of propane=((number of moles of propane supplied)−(number of moles of unreacted propane))/(number of moles of propane supplied)×100

Example 1

An oxide catalyst represented by the composition formula $Mo_1V_{0.19}Sb_{0.229}Nb_{0.109}W_{0.03}Ce_{0.008}$ was prepared according to the following method.
(Preparation Step) Aqueous Mixed Liquid (A')

To 1669 g of water, 490.8 g of ammonium heptamolybdate $[(NH_4)_6Mo_7O_{24}\cdot 4H_2O]$, 61.4 g of ammonium metavanadate $[NH_4VO_3]$, 92.7 g of diantimony trioxide $[Sb_2O_3]$, and 9.8 g of cerium nitrate $[Ce(NO_3)_3\cdot 6H_2O]$ were added and heated at 95° C. for 1 hour while being stirred to prepare an aqueous mixed liquid (A').

To 487.9 g of an aqueous mixed liquid ($N_0$) having a molar ratio of oxalic acid/niobium of 2.340, 67.6 g of hydrogen peroxide water containing 30% by mass of $H_2O_2$ was added, and a resultant mixture was stirred and mixed at room temperature for 10 minutes to prepare an aqueous mixed liquid ($N_1$). The molar ratio in terms of $H_2O_2$/Nb in the aqueous mixed liquid ($N_1$) was 2. The result is shown in Table 1.
(Mixing Step) Aqueous Mixed Liquid (B)

The resultant aqueous mixed liquid (A') was cooled to 70° C., thereafter to the aqueous mixed liquid, 897.4 g of silica sol containing 34.1% by mass of $SiO_2$ and 0.3% by mass of $NH_3$ was added, further, 108.0 g of hydrogen peroxide water containing 30% by mass of $H_2O_2$ was added, and stirring was continued at 60° C. for 1 minute. Next, the whole amount of the aqueous mixed liquid ($N_1$), 38.2 g of ammonium metatungstate aqueous solution (purity of 50%), and a dispersion liquid obtained by dispersing 294.0 g of powdery silica in 2646.0 g of water were added in sequence to the aqueous mixed liquid (A'). The oxidation-reduction potential on that occasion (at the point in time when the target period started) was measured with an ORP electrode (HM-31P, manufactured by DKK-TOA CORPORATION) to find that the value was the same as the value of the potential of the standard liquid described in Comparative Example 1, which will be described later.
(Aging Step)

An aqueous mixed liquid (B) in the form of a slurry was obtained by adding 20.3 g of 25% ammonia water 1 minute after the measurement and subjecting a resultant mixture to aging by stirring at 60° C. for 2 hours. The molar ratio in terms of $NH_3$/Nb in the aqueous mixed liquid (B) was 1.5. The oxidation-reduction potential 30 minutes after the point in time when the target period started (at the point in time when the target period ended) was measured to calculate a value (potential difference from standard liquid) which is obtained by subtracting the oxidation-reduction potential from the potential, at the same point in time, of the standard liquid which was subjected to aging under the same conditions as those in Comparative Example 1. In addition, the amount of potential dropped in the target period was calculated by subtracting the potential at the point in time when the target period ended from the potential at the point in time when the target period started. The results are shown in Table 1.

(Drying Step) Dried Powder (C)

The resultant aqueous mixed liquid (B) was supplied to a centrifugal spray drier (the heat source for drying is air, and the same heat source for drying was used in the following centrifugal spray driers) to be dried to obtain a fine, spherical dried powder (C). The temperature at the inlet of the drier was 210° C., and the temperature at the outlet was 120° C.

The resultant dried powder (C) was classified using a sieve having an opening of 25 μm to obtain a dried powder (D) being a classified product. The average primary particle diameter was 54 μm. The average particle diameter was measured with "LS230," trade name, manufactured by Beckman Coulter, Inc. (the following average particle diameters were measured in the same manner).
(Calcination Step) Oxide Catalyst (E)

The resultant dried powder (D) was supplied to a continuous SUS cylindrical calcination pipe having a diameter (inner diameter; the following diameters were the same) of 3 inches and a length of 89 cm at a supply rate of 80 g/hr in a rotary furnace. Into the calcination pipe, a nitrogen gas of 1.5 NL/min was allowed to flow in each of the direction opposite to the direction of supplying the dried powder (namely countercurrent; the same applies to the following directions opposite) and the same direction as the direction of supplying the dried powder (namely, parallel current; the same applies to the following same directions) to make the total flow rate 3.0 NL/min. The pre-stage calcination was performed by setting the temperature of the furnace such that the temperature can be raised to 360° C. being the highest calcination temperature in 4 hours while the calcination pipe was rotated at a rate of 4 revolutions/min, and the temperature can be held at 360° C. for 1 hour. A small amount of the pre-stage calcined body collected at the outlet of the calcination pipe was sampled and heated to 400° C. in a nitrogen atmosphere, and thereafter the reduction rate was measured and found to be 10.1%. The collected pre-stage calcined body was supplied to a continuous SUS calcination pipe having a diameter of 3 inches and a length of 89 cm at a supply rate of 60 g/hr in a rotary furnace. Into the calcination pipe, a nitrogen gas of 1.1 NL/min was allowed to flow in each of the direction opposite to the direction of supplying the dried powder and the same direction as the direction of supplying the dried powder to make the total flow rate 2.2 NL/min. The main calcination was performed by setting the temperature of the furnace such that the temperature can be raised to 680° C. in 2 hours, held at 680° C. for 2 hours, and thereafter lowered to 600° C. in 8 hours, and thus an oxide catalyst (E) was obtained.
(Removal Step)

Into a perpendicular tube (inner diameter of 41.6 mm, length of 70 cm), which is provided with a holed disk at the bottom portion thereof, the holed disk including 3 holes having a diameter of 1/64 inches, and which has a paper filter installed at the upper portion thereof, 50 g of the oxide catalyst (E) was loaded. Subsequently, air was circulated upward from below via each hole of the perpendicular tube at room temperature to facilitate contact among calcined bodies. The length of the air current on that occasion in the flowing direction of the air current was 56 mm, and the average linear velocity of the air current was 332 m/s. A protrusion did not exist in the oxide catalyst (E) obtained after 24 hours.
(Production Step) Ammoxidation Reaction of Propane Propane was subjected to a gas-phase catalytic ammoxidation reaction according to the following method using the oxide catalyst (E) obtained above. In a Vycor glass fluidized bed type reaction pipe having an inner diameter of 25 mm, 38 g of the oxide catalyst was filled, and a mixed gas having a molar ratio of propane:ammonia:oxygen:helium=1:1:2.9:18 was supplied at a contact time of 3.0 (sec·g/cm³), reaction temperature of 445° C., and a reaction pressure of 40 kPa. The reaction yield of acrylonitrile (AN), the potential difference from the standard liquid, and the amount of potential dropped each obtained when the reaction was performed for consecutive 10 days with respect to this oxide catalyst are shown in Table 1.

Examples 2 to 4

An oxide catalyst was produced in the same manner as in Example 1 except that the amount of ammonia water added in Example 1 was changed to the amount described in Table 1. The potential difference from the standard liquid and the amount of potential dropped were also measured in the same manner as in Example 1. The reaction yield of acrylonitrile (AN), the potential difference from the standard liquid, and the amount of potential dropped each obtained when the ammoxidation reaction of propane was performed in the same manner as in Example 1 with respect to this oxide catalyst are shown in Table 1.

Examples 5 and 6

An oxide catalyst was produced in the same manner as in Example 1 except that the aqueous mixed liquid ($N_1$), the ammonium metatungstate aqueous solution, and the dispersion liquid obtained by dispersing powdery silica in water were added in sequence to the aqueous mixed liquid (A'), thereafter the resultant mixture was subjected to aging by stirring at the temperature described in Table 1 and for the time described in Table 1, and an aqueous mixed liquid (B) in the form of a slurry was obtained without adding ammonia water. The potential difference from the standard liquid and the amount of potential dropped were also measured in the same manner as in Example 1. The reaction yield of acrylonitrile (AN), the potential difference from the standard liquid, and the amount of potential dropped each obtained when the ammoxidation reaction of propane was performed in the same manner as in Example 1 with respect to this oxide catalyst are shown in Table 1.

Examples 7 and 8

An oxide catalyst was produced in the same manner as in Example 1 except that the amount of hydrogen peroxide water added to the Nb mixed liquid was changed to the value in Table 1, and an aqueous mixed liquid (B) in the form of a slurry was obtained without adding ammonia water. The potential difference from the standard liquid and the amount of potential dropped were measured at the potential between 90 minutes and 120 minutes after the start of aging. The reaction yield of acrylonitrile (AN), the potential difference from the standard liquid, and the amount of potential dropped each obtained when the ammoxidation reaction of propane was performed in the same manner as in Example 1 with respect to this oxide catalyst are shown in Table 1.

Examples 9 to 11

An oxide catalyst was produced in the same manner as in Example 1 except that the amount of addition of hydrogen peroxide to the niobium mixed liquid, and the temperature and the time of aging were changed to the values shown in Table 1. The potential difference from the standard liquid and the amount of potential dropped were measured at the potential between 90 minutes and 120 minutes after the start of aging. The reaction yield of acrylonitrile (AN), the potential difference from the standard liquid, and the amount of potential dropped each obtained when the ammoxidation reaction of propane was performed in the same manner as in Example 1 with respect to this oxide catalyst are shown in Table 1.

Example 12

An oxide catalyst was produced in the same manner as in Example 1 except that the addition of ammonia water was changed to be carried out 30 minutes after adding the dispersion liquid obtained by dispersing powdery silica in water to the aqueous mixed liquid (A'). The potential difference from the standard liquid and the amount of potential dropped were measured for 30 minutes from the time immediately before adding ammonia water till 30 minutes after that. The reaction yield of acrylonitrile (AN), the potential difference from the standard liquid, and the amount of potential dropped each obtained when the ammoxidation reaction of propane was performed in the same manner as in Example 1 with respect to this oxide catalyst are shown in Table 1.

Example 13

An oxide catalyst was produced in the same manner as in Example 1 except that the addition of ammonia water was changed to be carried out 60 minutes after adding the dispersion liquid obtained by dispersing powdery silica in water to the aqueous mixed liquid (A'). The potential difference from the standard liquid and the amount of potential dropped were measured for 30 minutes from the time immediately before adding ammonia water till 30 minutes after that. The reaction yield of acrylonitrile (AN), the potential difference from the standard liquid, and the amount of potential dropped each obtained when the ammoxidation reaction of propane was performed in the same manner as in Example 1 with respect to this oxide catalyst are shown in Table 1.

Example 14

An oxide catalyst was produced in the same manner as in Example 1 except that the addition of ammonia water was changed to be carried out after adding silica sol to the aqueous mixed liquid (A'). The reaction yield of acrylonitrile (AN), the potential difference from the standard liquid, and the amount of potential dropped each obtained when the ammoxidation reaction of propane was performed in the same manner as in Example 1 with respect to this oxide catalyst are shown in Table 1.

Comparative Example 1

An oxide catalyst was produced in the same manner as in Example 1 except that ammonia water in Example 1 was not added, and the temperature of aging in Example 1 was changed to 55° C. That is, the aqueous mixed liquid which is prepared in Comparative Example 1 corresponds to the standard liquid in Examples 1 to 16. The amount of potential dropped was also measured in the same manner as in Example 1. The reaction yield of acrylonitrile (AN) and the amount of potential dropped each obtained when the ammoxidation reaction of propane was performed in the same manner as in Example 1 with respect to this oxide catalyst are shown in Table 1. In the preparation step and the aging step of Comparative Example 1, the evaluation was such that an influence of added hydrogen peroxide was large, and therefore precipitation of Nb was not facilitated.

Comparative Example 2

An oxide catalyst was produced in the same manner as in Example 1 except that the temperature of aging in Example 1 was changed to 30° C. The amount of potential dropped was also measured in the same manner as in Example 1. The reaction yield of acrylonitrile (AN) and the amount of potential dropped each obtained when the ammoxidation reaction of propane was performed in the same manner as in Example 1 with respect to this oxide catalyst are shown in Table 1.

Example 15

An oxide catalyst was produced in the same manner as in Example 1 except that the amount of ammonia water added in Example 1 was changed to the amount described in Table 1. The potential difference from the standard liquid and the amount of potential dropped were also measured in the same manner as in Example 1. The reaction yield of acrylonitrile (AN), the potential difference from the standard liquid, and the amount of potential dropped each obtained when the ammoxidation reaction of propane was performed in the same manner as in Example 1 with respect to this oxide catalyst are shown in Table 1.

Example 16

An oxide catalyst was produced in the same manner as in Example 1 except that the aging temperature in Example 1 was changed to the temperature described in Table 1. The potential difference from the standard liquid and the amount of potential dropped were also measured in the same manner as in Example 1. The reaction yield of acrylonitrile (AN), the potential difference from the standard liquid, and the amount of potential dropped each obtained when the ammoxidation reaction of propane was performed in the same manner as in Example 1 with respect to this oxide catalyst are shown in Table 1.

Example 17

An oxide catalyst was produced in the same manner as in Example 1 except that a catalyst was prepared in such a way as to have a composition $Mo_1V_{0.210}Sb_{0.259}Nb_{0.109}W_{0.03}Ce_{0.005}$ by performing the preparation step and the mixing step as described below.
(Preparation Step) Aqueous Mixed Liquid (A')
To 1807 g of water, 479.7 g of ammonium heptamolybdate [$(NH_4)_6Mo_7O_{24} \cdot 4H_2O$], 66.3 g of ammonium metavanadate [$NH_4VO_3$], 102.4 g of diantimony trioxide [$Sb_2O_3$], and 6.0 g of cerium nitrate [$Ce(NO_3)_3 \cdot 6H_2O$] were added and heated at 95° C. for 1 hour while being stirred to prepare an aqueous mixed liquid (A').
To 454.8 g of an aqueous mixed liquid ($N_0$) having a molar ratio of oxalic acid/niobium of 2.340, 67.6 g of hydrogen peroxide water containing 30% by mass of $H_2O_2$ was added, and a resultant mixture was stirred and mixed at room temperature for 10 minutes to prepare an aqueous mixed liquid ($N_1$).

(Mixing Step) Aqueous Mixed Liquid (B)
The resultant aqueous mixed liquid (A') was cooled to 70° C., thereafter to the aqueous mixed liquid, 897.4 g of silica sol containing 34.1% by mass of $SiO_2$ and 0.3% by mass of $NH_3$ was added, further, 119.3 g of hydrogen peroxide water containing 30% by mass of $H_2O_2$ was added, and stirring was continued at 60° C. for 1 minute. Next, the whole amount of the aqueous mixed liquid ($N_1$), 37.4 g of ammonium metatungstate aqueous solution (purity of 50%), and a dispersion liquid obtained by dispersing 294.0 g of powdery silica in 2646.0 g of water were added in sequence to the aqueous mixed liquid (A'). The oxidation-reduction potential on that occasion (at the point in time when the target period started) was measured with an ORP electrode (HM-31P, manufactured by DKK-TOA CORPORATION).
(Aging Step)
An aqueous mixed liquid (B) in the form of a slurry was obtained by adding 20.3 g of 25% ammonia water 1 minute after the measurement and subjecting a resultant mixture to aging by stirring at 60° C. for 2 hours. The molar ratio in terms of $NH_3/Nb$ in the aqueous mixed liquid (B) was 1. The potential difference from the standard liquid and the amount of potential dropped were also measured in the same manner as in Example 1. The reaction yield of acrylonitrile (AN), the potential difference from the standard liquid, and the amount of potential dropped each obtained when the ammoxidation reaction of propane was performed in the same manner as in Example 1 with respect to this oxide catalyst are shown in Table 1.

Comparative Example 3

An oxide catalyst was produced in the same manner as in Example 1 except that ammonia water in Example 17 was not added, and the temperature of aging in Example 17 was changed to 55° C. That is, an aqueous mixed liquid which is prepared in Comparative Example 3 corresponds to the standard liquid in Example 17. The potential difference from the standard liquid and the amount of potential dropped were also measured in the same manner as in Example 1. The reaction yield of acrylonitrile (AN), the potential difference from the standard liquid, and the amount of potential dropped each obtained when the ammoxidation reaction of propane was performed in the same manner as in Example 1 with respect to this oxide catalyst are shown in Table 1.

Example 18

An oxide catalyst was produced in the same manner as in Example 1 except that a catalyst was prepared in such a way as to have a composition $Mo_1V_{0.190}Sb_{0.257}Nb_{0.110}W_{0.03}Ce_{0.005}$ by performing the preparation step and the mixing step as described below.
(Preparation Step) Aqueous Mixed Liquid (A')
To 1640 g of water, 482.7 g of ammonium heptamolybdate [$(NH_4)_6Mo_7O_{24} \cdot 4H_2O$], 60.4 g of ammonium metavanadate [$NH_4VO_3$], 101.7 g of diantimony trioxide [$Sb_2O_3$], and 6.0 g of cerium nitrate [$Ce(NO_3)_3 \cdot 6H_2O$] were added and heated at 95° C. for 1 hour while being stirred to prepare an aqueous mixed liquid (A').
To 488.7 g of an aqueous mixed liquid ($N_0$) having a molar ratio of oxalic acid/niobium of 2.340, 67.7 g of hydrogen peroxide water containing 30% by mass of $H_2O_2$ was added, and a resultant mixture was stirred and mixed at room temperature for 10 minutes to prepare an aqueous mixed liquid ($N_1$).

(Mixing Step) Aqueous Mixed Liquid (B)

The resultant aqueous mixed liquid (A') was cooled to 70° C., thereafter to the aqueous mixed liquid, 897.4 g of silica sol containing 34.1% by mass of $SiO_2$ and 0.3% by mass of $NH_3$ was added, further, 118.4 g of hydrogen peroxide water containing 30% by mass of $H_2O_2$ was added, and stirring was continued at 60° C. for 1 minute. Next, the whole amount of the aqueous mixed liquid ($N_1$), 37.4 g of ammonium metatungstate aqueous solution (purity of 50%), and a dispersion liquid obtained by dispersing 294.0 g of powdery silica in 2646.0 g of water were added in sequence to the aqueous mixed liquid (A'). The oxidation-reduction potential on that occasion (at the point in time when the target period started) was measured with an ORP electrode (HM-31P, manufactured by DKK-TOA CORPORATION).

(Aging Step)

An aqueous mixed liquid (B) in the form of a slurry was obtained by adding 20.3 g of 25% ammonia water 1 minute after the measurement and subjecting a resultant mixture to aging by stirring at 60° C. for 2 hours. The molar ratio in terms of $NH_3$/Nb in the aqueous mixed liquid (B) was 1. The potential difference from the standard liquid and the amount of potential dropped were also measured in the same manner as in Example 1. The reaction yield of acrylonitrile (AN), the potential difference from the standard liquid, and the amount of potential dropped each obtained when the ammoxidation reaction of propane was performed in the same manner as in Example 1 with respect to this oxide catalyst are shown in Table 1.

Comparative Example 4

An oxide catalyst was produced in the same manner as in Example 1 except that ammonia water in Example 18 was not added, and the temperature of aging in Example 18 was changed to 55° C. That is, an aqueous mixed liquid which is prepared in Comparative Example 4 corresponds to the standard liquid in Example 18. The potential difference from the standard liquid and the amount of potential dropped were also measured in the same manner as in Example 1. The reaction yield of acrylonitrile (AN), the potential difference from the standard liquid, and the amount of potential dropped each obtained when the ammoxidation reaction of propane was performed in the same manner as in Example 1 with respect to this oxide catalyst are shown in Table 1.

Comparative Example 5

An oxide catalyst was produced in the same manner as in Comparative Example 1 except that the aging time was changed from 2 hours to 4 hours. The potential difference from the standard liquid and the amount of potential dropped were also measured in the same manner as in Example 1. That is, an aqueous mixed liquid which is prepared in Comparative Example 1 corresponds to the standard liquid in Comparative Example 5. The reaction yield of acrylonitrile (AN), the potential difference from the standard liquid, and the amount of potential dropped each obtained when the ammoxidation reaction of propane was performed in the same manner as in Example 1 with respect to this oxide catalyst are shown in Table 1. It is to be noted that the amount of potential dropped after 4 hours was 15 mV.

TABLE 1

| | $NH_3$ addition $NH_3$/Nb | Amount of addition of ammonia water (g) | Aging temperature | Amount of $H_2O_2$ $H_2O_2$/Nb | Amount of $H_2O_2$ water added to Nb mixed liquid (g) | Aspect of facilitation of precipitation of Nb | AN yield/% | (Potential of standard liquid)-(potential of sample for measurement) (mV) Point in time when target period started | (Potential of standard liquid)-(potential of sample for measurement) (mV) Point in time when target period ended | Amount (mV) of potential dropped in target Period | Requirement (a) and/or (b) |
|---|---|---|---|---|---|---|---|---|---|---|---|
| Example 1 | 1.5 | 20.3 | 60° C. | 2 | 67.6 | (I) | 55.5 | 0 | 13 | 18 | (b) |
| Example 2 | 3 | 50.7 | 60° C. | 2 | 67.6 | (I) | 55.2 | 0 | 25 | 30 | (b) |
| Example 3 | 5.3 | 97.3 | 60° C. | 2 | 67.6 | (I) | 55.0 | 0 | 35 | 40 | (b) |
| Example 4 | 1 | 10.1 | 60° C. | 2 | 67.6 | (I) | 55.2 | 0 | 9 | 14 | (b) |
| Example 5 | 0.5 | 0 | 68° C. | 2 | 67.6 | (II) | 55.1 | 0 | 23 | 28 | (b) |
| Example 6 | 0.5 | 0 | 75° C. | 2 | 67.6 | (II) | 54.9 | 0 | 28 | 33 | (b) |
| Example 7 | 0.5 | 0 | 60° C. | 0.1 | 3.4 | (III) | 55.4 | 40 | 40 | 5 | (a) |
| Example 8 | 0.5 | 0 | 60° C. | 0 | 0 | (III) | 55.3 | 45 | 55 | 15 | (a) and (b) |
| Example 9 | 1.5 | 20.3 | 68° C. | 0 | 0 | (I), (II), (III) | 55.0 | 45 | 95 | 15 | (a) and (b) |
| Example 10 | 1.5 | 20.3 | 60° C. | 0.1 | 3.4 | (I), (III) | 55.6 | 40 | 60 | 25 | (a) and (b) |
| Example 11 | 1.5 | 20.3 | 68° C. | 0.1 | 3.4 | (I), (II), (III) | 55.1 | 40 | 80 | 45 | (a) and (b) |
| Example 12 | 1.5 | 20.3 | 60° C. | 2 | 67.6 | (I) | 55.2 | 0 | 35 | 40 | (b) |
| Example 13 | 1.5 | 20.3 | 60° C. | 2 | 67.6 | (I) | 54.9 | 0 | 55 | 60 | (b) |
| Example 14 | 1.5 | 20.3 | 60° C. | 2 | 67.6 | (I) | 54.7 | 30 | 50 | 20 | (a) and (b) |
| Example 15 | 6.5 | 121.6 | 60° C. | 2 | 67.6 | (I) | 54.2 | 0 | 45 | 50 | (b) |
| Example 16 | 1.5 | 20.3 | 52° C. | 2 | 67.6 | (I) | 54.3 | 0 | 27 | 32 | (b) |
| Comparative Example 1 | 0.5 | 0 | 55° C. | 2 | 67.6 | — | 53.5 | — | — | 5 | — |
| Comparative Example 2 | 1.5 | 20.3 | 30° C. | 2 | 67.6 | — | 53.6 | 0 | 0 | 5 | — |
| Example 17 | 1.7 | 20.3 | 60° C. | 2 | 67.6 | (I) | 54.5 | −1 | 14 | 20 | (b) |
| Comparative Example 3 | 0.6 | 0 | 55° C. | 2 | 67.6 | — | 52.7 | — | — | 5 | — |
| Example 18 | 1.5 | 20.3 | 60° C. | 2 | 67.6 | (I) | 55.0 | 2 | 14 | 17 | (a) and (b) |
| Comparative Example 4 | 0.5 | 0 | 55° C. | 2 | 67.6 | — | 52.9 | — | — | 6 | — |
| Comparative Example 5 | 0.5 | 0 | 55° C. | 2 | 67.6 | — | 53.9 | 0 | 0 | 5 | — |

The "Aspect of facilitation" in Table 1 shows which of aspects (I) to (III) in the present embodiment each Example corresponds to. It is to be noted that when a plurality of aspects are satisfied, the aspects are shown together, and "–" means that the Example does not correspond to any of the aspects.

In addition, the "Requirement (a) or (b)" in Table 1 shows which of the requirements (a) and (b) in the present embodiment each Example satisfies. It is to be noted that when both of the requirements are satisfied, the requirements are shown together, and "–" means that neither of the requirements is satisfied.

The present application claims the priority based on Japanese Patent Application (Japanese Patent Application No. 2016-178885) filed on Sep. 13, 2016, the contents of which are incorporated herein by reference.

INDUSTRIAL APPLICABILITY

The method for producing an oxide catalyst according to the present invention can be used for production of a catalyst for producing an unsaturated nitrile.

The invention claimed is:

1. A method for producing an unsaturated nitrile, the method comprising the steps of:
producing an oxide catalyst by following steps of:
a raw material preparation step of obtaining an aqueous mixed liquid comprising Mo, V, Sb, and Nb;
an aging step of subjecting the aqueous mixed liquid to aging at more than 30° C.;
a drying step of drying the aqueous mixed liquid, thereby obtaining a dried powder; and
a calcination step of calcining the dried powder, thereby obtaining the oxide catalyst,
wherein, in the raw material preparation step and/or the aging step, precipitation of Nb is facilitated by performing at least one operation selected from the group consisting of the following (I) to (III):
(I) in the raw material preparation step, the aqueous mixed liquid is prepared by mixing a Nb raw material liquid comprising Nb with a MoVSb raw material liquid comprising Mo, V, and Sb, wherein ammonia is added to at least one of the MoVSb raw material liquid, the Nb raw material liquid, and the aqueous mixed liquid such that a molar ratio in terms of $NH_3/Nb$ in the aqueous mixed liquid is adjusted to be 0.7 or more, and in the aging step, a temperature of the aqueous mixed liquid is adjusted to more than 60° C.;
(II) in the aging step, a temperature of the aqueous mixed liquid is adjusted to more than 65° C.; and
(III) in the raw material preparation step, the aqueous mixed liquid is prepared by mixing a Nb raw material liquid comprising Nb with a MoVSb raw material liquid comprising Mo, V, and Sb, wherein a molar ratio in terms of $H_2O_2/Nb$ in the Nb raw material liquid is adjusted to less than 0.2, and in the aging step, a temperature of the aqueous mixed liquid is adjusted to more than 60° C.; and
further comprising a step of producing an unsaturated nitrile through a gas-phase catalytic ammoxidation reaction of propane or isobutane in a presence of the produced oxide catalyst.

2. The method for producing an unsaturated nitrile according to claim 1, wherein
the oxide catalyst has a composition represented by the following formula (1):

$$MoV_aSb_bNb_cZ_dO_n \quad (1)$$

wherein Z represents at least one element selected from the group consisting of W, La, Ce, Yb, and Y; a, b, c, and d represent values in ranges of $0.01 \le a \le 0.35$, $0.01 \le b \le 0.35$, $0.01 \le c \le 0.20$, and $0.00 \le d \le 0.10$, respectively; and n represents a value satisfying a balance of atomic valences.

3. The method for producing an unsaturated nitrile according to claim 1, wherein
the oxide catalyst comprises 30% by mass or more and 70% by mass or less of a carrier based on a total amount of the oxide catalyst.

\* \* \* \* \*